US00PP21071P3

(12) United States Plant Patent
Meilland

(10) Patent No.: US PP21,071 P3
(45) Date of Patent: Jun. 22, 2010

(54) FLORIBUNDA ROSE PLANT NAMED 'MEIRYSETT'

(50) Latin Name: *Rosa hybrida*
Varietal Denomination: Meirysett

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/314,186

(22) Filed: Dec. 5, 2008

(65) Prior Publication Data

US 2010/0095413 P1 Apr. 15, 2010

(30) Foreign Application Priority Data

Oct. 13, 2008 (QZ) ..... PBR 2008/2249

(51) Int. Cl.
*A01H 5/00* (2006.01)

(52) U.S. Cl. ..... Plt./141

(58) Field of Classification Search ..... Plt./141
See application file for complete search history.

*Primary Examiner*—Annette H Para
(74) *Attorney, Agent, or Firm*—Buchanan Ingersoll & Rooney PC

(57) ABSTRACT

A new and distinct Floribunda rose plant is provided which forms in abundance attractive blossoms that are deep greyed-purple on the upper surface and ocher yellow on the under surface. Such flower coloration is considered to be rather unusual. The greyed-purple petal coloration on the upper surface is so dark that it sometimes appears to be almost black upon casual observation. The plant exhibits strong vegetation, a semi-erect growth habit, and dark green foliage with a glossy upper surface. The disease tolerance is good particularly with respect to Oidium. The new variety is well suited for growing as attractive ornamentation in parks and gardens.

1 Drawing Sheet

Botanical/commercial classification: *Rosa hybrida*/Floribunda Rose Plant

Varietal denomination: cv. Meirysett

SUMMARY OF THE INVENTION

Figures 1, 2, 3, 4, 5, 6, 7, 8, 9, 10, 11, 12, 13, 14, 15, 16:
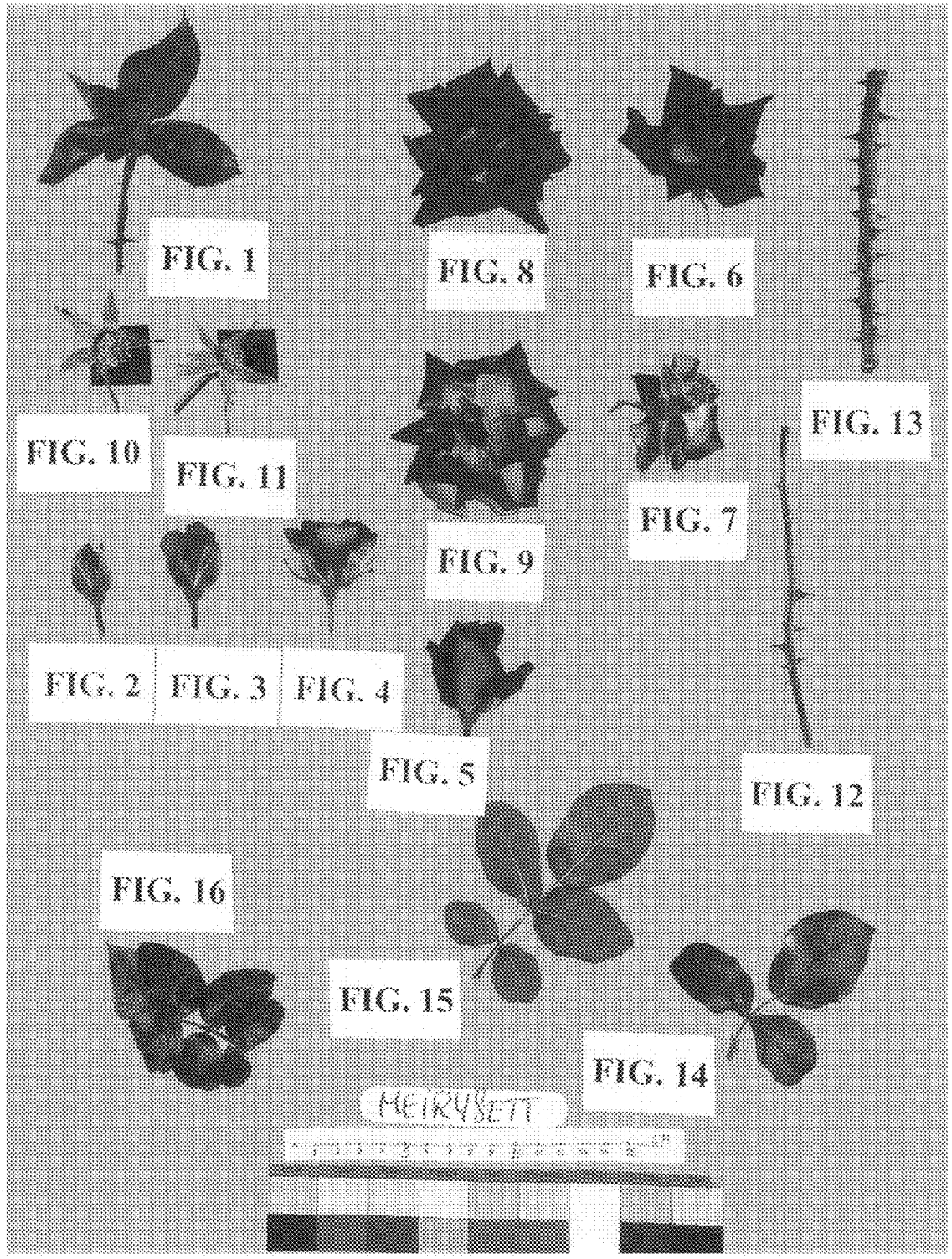

The new variety of *Rosa hybrida* Floribunda rose plant was created by artificial pollination wherein two parents were crossed which previously had been studied in the hope that they would contribute the desired characteristics. The female parent (i.e., the seed parent) was a product of the cross of the 'Mme A. Meilland' variety (non-patented in the United States) and the 'Meipsilon' variety (non-patented in the United States). The male parent (i.e., the pollen parent) was the 'Delepi' variety (non-patented in the United States). The 'Mme A. Meilland' variety sometimes is known as the 'Climbing Peace' variety. The 'Meipsilon' variety is marketed under the YAKIMOUR trademark, and the 'Delepi' variety is marketed under the EPIDOR trademark. The parentage of the new variety can be summarized as follows:

('Mme A. Meilland' ×'Meipsilon') ×'Delepi'.

The seeds resulting from the above pollination were sown and small plants were obtained which were physically and biologically different from each other. Selective study resulted in the identification of a single plant of the new variety.

It was found that the new Floribunda rose plant of the present invention:

(a) exhibits a semi-erect growth habit, (b) abundantly forms attractive blossoms that are deep greyed-purple on the upper surface and ocher yellow on the under surface, (c) forms attractive dark green foliage that is glossy on the upper surface, (d) displays good tolerance to disease, and (e) is well suited for growing as ornamentation in parks and gardens.

The new variety well meets the needs of the horticultural industry and can be grown to advantage in the landscape where attractive ornamentation is desired. The flower coloration is considered to be rather unusual. The greyed-purple petal coloration on the upper surface is so dark that is sometimes appears to be almost black upon casual inspection.

The new variety can be readily distinguished from its ancestors. For instance, the blossoms of the 'Mme A. Meilland' variety are golden yellow edged with rose pink. The 'Meipsilon' variety forms cherry-red blossoms with a pale yellow reverse. The 'Delepi' variety forms deep yellow blossoms.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'Meirysett'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately two years of age and were observed during October while budded on *Rosa laxa* understock and growing outdoors at Le Cannet des Maures, Var, France. Dimensions in centimeters are indicated at the bottom of the photograph together with comparative color information.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart), London, England. Common color terms are to be accorded their customary dictionary significance. The description is based on the observation of two-year-old plants during May while budded on Rosa laxa understock and outdoors at Le Cannet des Maures, Var, France.

Class: Floribunda.

Plant:

*Habit.*—Semi-erect.

Branches:

*Color.*—Young stems: near Green Group 143A. adult wood: near Green Group 143B.

*Thorns.*—On young stems: small prickles: commonly absent. long prickles: configuration: very elongated and longish-pointed on the upper surface, hooked on the under surface, and with a broad ovate and long base. quantity: approximately 9 on average on a stem length of 10 cm. length: approximately 1 cm on average. color near Greyed-Orange Group 164C. on adult stems: small prickles: commonly absent. long prickles: configuration: very elongated and very longish-pointed on the upper surface, hooked on the under surface, and with a broad, ovate and long base. quantity: approximately 14 on average on a stem length of 18 cm. length: approximately 1 cm on average. color near Greyed-Orange Group 164C.

Leaves:

*Stipules.*—Adnate, pectinate, and rather broad, approximately 1.7 cm in length on average, approximately 0.5 cm in width on average, near Yellow-Green Group 146B on the upper surface, and near Yellow-Green Group 146A on the under surface.

*Petioles.*—Upper surface: near Greyed-Purple Group 183A in coloration. under surface: near Yellow-Green Group 152A in coloration. texture: non-glandular and commonly without prickles. length: approximately 2.8 cm for the terminal leaflet.

*Rachis.*—Upper surface: near Greyed-Purple Group 183A in coloration. under surface: near Yellow-Green Group 152A in coloration. texture: generally smooth.

*Leaflets.*—Number: 3, 5 (most often), and 7. shape: generally oval with a rounded base and an acuminate tip. size: the terminal leaflets commonly are approximately 5 cm in length on average, and approximately 3 cm in width on average. serration: small and single (as illustrated). texture: somewhat thick and glossy on the upper surface. general appearance: rather dense. color (young foliage): upper surface: near Green Group 139A. under surface: near Yellow-Green Group 146B. color (adult foliage): upper surface: near Green Group 135A. under surface: near Yellow-Green Group 147B.

Inflorescence:

*Number of flowers.*—Commonly one flower per stem.

*Peduncle.*—Glandular, near Yellow-Green Group 146C and more or less suffused with near Greyed-Orange Group 176A in coloration, approximately 4.3 cm in length on average, and approximately 0.3 cm in diameter on average.

*Sepals.*—Upper surface: tomentose and near Green Group 138B in coloration. under surface: smooth and near Yellow-Green Group 143A in coloration. configuration: approximately 3.4 cm in length on average, approximately 1 cm in width on average at the widest point, and longish and narrow with an upright base.

*Buds.*—Shape: elongated. size: medium. length: approximately 2 cm on average. width: approximately 1.8 cm on average at the widest point. color. upper surface: near Greyed-Purple Group 183A as the calyx breaks. under surface: near Orange-Red Group 31C as the calyx breaks.

*Flower.*—Shape: flat cup-shaped. diameter: approximately 9.5 cm on average when fully open. color (in the course of opening): upper surface: near Greyed-Purple Group 185A. under surface: near Yellow-Orange Group 22B suffused with Orange-Red Group 31C. color (when fully open): upper surface: near Greyed-Purple Group 185B. under surface: near Yellow-Orange Group 16B suffused with Orange-Red Group 31C. fragrance: none. petal number commonly approximately 37 to 40 on average under normal growing conditions. petal shape: generally with a rounded tip and a somewhat pointed base. petal size: commonly approximately 3.7 cm in length on average, and approximately 3.3 cm in width on average. petal texture: flexible. petal arrangement: imbricated, and without petaloids. petal drop: good with the petals commonly detaching cleanly before drying. stamen number approximately 138 on average. anthers: regularly arranged around the styles, approximately 0.3 cm in size on average, and near Yellow-Orange Group 20A in coloration. pollen: present. filaments: approximately 1 cm in length on average, and near Red Group 40A in coloration. pistils: approximately 89 on average. stigmas: approximately 0.2 cm in size on average, and near Yellow Group 12C in coloration. styles: approximately 0.6 cm in length on average, and near Yellow Group 4D in coloration. receptacle: smooth, pitcher-shaped in longitudinal section, approximately 0.8 cm in length on average, approximately 0.9 cm in width on average at the widest point, and near Yellow-Green Group 146A and more or less suffused with Greyed-Orange Group 176A in coloration.

Development:

*Vegetation.*—Strong.

*Blooming.*—Medium season, very abundant and substantially continuous.

*Tolerance to diseases.*—Good, particularly with respect to Oidium.

*Tolerance to drought and cold.*—No particular tolerance to drought and cold has been observed for the new variety with the tolerance being generally comparable to that of commercially available ornamental Floribunda rose plants typically grown in parks and gardens.

I claim:

1. A new and distinct Floribunda rose plant characterized by the following combination of characteristics:

(a) exhibits a semi-erect growth habit, (b) abundantly forms attractive blossoms that are deep greyed-purple on the upper surface and ocher yellow on the under surface, (c) forms attractive dark green foliage that is glossy on the upper surface, (d) displays excellent tolerance to disease, and (e) is well suited for growing as ornamentation in parks and gardens; substantially as herein shown and described.

* * * * *

MEIRYSETT